(12) United States Patent
Tsoukalis

(10) Patent No.: US 10,058,652 B2
(45) Date of Patent: Aug. 28, 2018

(54) INFUSION PUMP DEVICE

(71) Applicant: MICREL Medical Devices S.A., Gerakas (GR)

(72) Inventor: Achilleas Tsoukalis, Gerakas (GR)

(73) Assignee: Micrel Medical Devices S.A., Gerakas (GR)

( * ) Notice: Subject to any disclaimer, the term of this patent is extended or adjusted under 35 U.S.C. 154(b) by 836 days.

(21) Appl. No.: 14/516,112

(22) Filed: Oct. 16, 2014

(65) Prior Publication Data

US 2015/0112265 A1 Apr. 23, 2015

(30) Foreign Application Priority Data

Oct. 17, 2013 (GR) .............................. 20130100591

(51) Int. Cl.
| | |
|---|---|
| *A61M 5/168* | (2006.01) |
| *A61M 5/142* | (2006.01) |
| *A61M 5/162* | (2006.01) |
| *F04B 13/00* | (2006.01) |
| *F04B 43/12* | (2006.01) |
| *A61M 5/36* | (2006.01) |
| *A61M 5/165* | (2006.01) |
| *A61M 5/155* | (2006.01) |

(52) U.S. Cl.
CPC .... *A61M 5/16822* (2013.01); *A61M 5/14232* (2013.01); *A61M 5/162* (2013.01); *F04B 13/00* (2013.01); *F04B 43/1253* (2013.01); *A61M 5/14244* (2013.01); *A61M 5/155* (2013.01); *A61M 5/16854* (2013.01); *A61M 5/365* (2013.01); *A61M 2005/1623* (2013.01); *A61M 2005/1657* (2013.01); *A61M 2005/16868* (2013.01); *A61M 2005/16872* (2013.01); *A61M 2205/215* (2013.01); *A61M 2205/7536* (2013.01); *A61M 2206/22* (2013.01)

(58) Field of Classification Search
CPC .......... A61M 5/16822; A61M 5/14232; A61M 5/162; A61M 5/14244; A61M 5/155; A61M 5/16854; A61M 5/365; A61M 2005/1623; A61M 2005/1657; A61M 2005/16868; A61M 2005/16872; A61M 2205/215; A61M 2205/7536; A61M 2206/22; F04B 43/1253; F04B 13/00
USPC .... 604/151, 131, 65–67; 128/DIG. 1, 12, 13
See application file for complete search history.

(56) References Cited

U.S. PATENT DOCUMENTS

| | | | | |
|---|---|---|---|---|
| 4,473,094 A | * | 9/1984 | Harris | A61M 5/162 137/550 |
| 5,304,165 A | * | 4/1994 | Haber | A61J 1/2089 604/411 |
| 5,980,490 A | | 11/1999 | Tsoukalis | |
| 9,044,542 B2 | * | 6/2015 | Patrick | A61B 8/00 |
| 2006/0245964 A1 | | 11/2006 | Koslov | |
| 2012/0016295 A1 | | 1/2012 | Tsoukalis | |

(Continued)

*Primary Examiner* — Manuel Mendez
(74) *Attorney, Agent, or Firm* — Hollingsworth Davis, LLC

(57) ABSTRACT

An infusion pump device comprises a pumping means having a fluid inlet which is adapted to be connected to a vial for taking fluid out of the vial and a fluid outlet which is adapted to be connected to an infusion catheter, and a controlling means which is adapted to be connected to the vial and to control pressure inside the vial so as to avoid occurrence of underpressure at the fluid inlet.

20 Claims, 4 Drawing Sheets

(56) References Cited

U.S. PATENT DOCUMENTS

2013/0079733 A1* 3/2013 Burt ..................... B05B 7/0012
604/290
2014/0081202 A1 3/2014 Tsoukalis

* cited by examiner

INFUSION PUMP DEVICE

BACKGROUND

The present invention relates to an infusion pump device comprising a pumping means having a fluid inlet which is adapted to be connected to a vial for taking fluid out of the vial and a fluid outlet which is adapted to be connected to an infusion catheter.

Known from the prior art are linear or rotary peristaltic pumps for infusion of drugs wherein a connection upstream directly or through a tubing and a spike is provided to a drug reservoir.

In medical practice, many drugs are supplied as fluids in glass vials, wherein subcutaneous infusions by pump require the steps of introducing air into the vial by a syringe so as to compress the air within the vial, then drawing up the drug into the same syringe, placing the syringe in a so-called syringe pump, and carrying out infusion using the syringe pump after having removed the needle and added a catheter or transferring the drug into a drug reservoir and carrying out infusion by means of a peristaltic pump once again through an appropriate catheter.

Such a procedure requires preparation and aseptic techniques which are difficult in particular for patients to employ at home when infusing immunoglobulin or other drugs.

Moreover, it is known that in both linear and rotary peristaltic pumps a negative pulse infusion or suction occurs during motion or rotation of a cam or rollers, at each alternation from a last to a first follower in linear peristaltic pumps, or at each alternation from one roller to the next roller in rotary peristaltic pumps. In order to replace conventional linear flow syringe pumps, for high accuracy pumps as described in e.g. U.S. Pat. No. 9,468,715 a completely pulseless linear flow is needed in accordance with a narrow trumpet curve as required by the IEC 60601-2-2 standard. In order to realize this, the provision of an extra cam and follower is suggested by U.S. Pat. No. 5,980,490 A or U.S. Pat. No. 7,645,127 for linear peristaltic pumps.

It is an object of the present invention to provide an infusion pump device with the simplest possible procedure for preparation and infusion.

It is a further object of the present invention to provide accuracy under worst case conditions and a linear flow in rotary peristaltic pumps.

SUMMARY

In order to achieve the above and further objects, according to a first aspect of the present invention, there is provided an infusion pump device comprising a pumping means having a fluid inlet which is adapted to be connected to a vial for taking fluid out of the vial and a fluid outlet which is adapted to be connected to an infusion catheter, and a controlling means which is adapted to be connected to the vial and to control pressure inside the vial so as to avoid occurrence of underpressure at the fluid inlet.

By providing the controlling means according to the present invention the occurrence of exceptional underpressure in the vial and, thus, in the upstream tubing during infusion is avoided which otherwise would degrade the accuracy of infusion. Since according to the teaching of the present invention the controlling means is adapted to control pressure inside the vial, in case of more viscous fluids the controlling means is also able to cause creation of overpressure in the vial to assist the more viscous fluids to be drawn out of the vial.

Further, by using the infusion pump device according to the present invention, a direct connection of the infusion mechanism to the vial can be provided throughout the infusion wherein the pumping means aspirates the drug directly from the vial. So, due to the present invention the procedure for the user is simplified and mainly requires only cleaning the opening or outlet of the vial, connecting the pumping means and the controlling means to the vial and then starting with the infusion.

In case of using spikes or needles, the pump aspirates the drug directly from the vial through a spike or needle which punctures a rubber bung closing the vial, wherein the procedure only requires the cleaning of the rubber bung, insertion of the spike or needle and then infusion and is, thus, very simple for the user. Other than an aspiration needle, consumables for this procedure only includes a subcutaneous infusion catheter, which in particular in the case of immunoglobulin may have more than one subcutaneous infusion needle which is called a "butterfly" or "octopus" embodiment.

The controlling means can provide a secondary air pressure equilibrating a vent path in one and the same spike or needle or in a separate spike or needle wherein the spikes are also known as air-vented spikes used for infusions from bigger bottles.

Further, in order to achieve the above or further objects, according to a second aspect of the present invention there is provided an infusion pump device, comprising a pumping means having a fluid inlet which is adapted to be connected to a vial for taking fluid out of the vial and a fluid outlet which is adapted to be connected to an infusion catheter, wherein the pumping means is a rotary peristaltic pump means comprising a stationary flexible, preferably resilient, first tubing which includes an inlet portion defining the fluid inlet and an outlet portion defining the fluid outlet and is provided between both the inlet and outlet portions with a bent portion having an essentially part-cycle, preferably half-cycle, form, and a rotor which is provided with engagement elements for locally engaging the bent portion of the first tubing so as to squeeze it during rotation for a pumping action, wherein the cross-section of the outlet portion of the first tubing is smaller than the cross-section of at least some initial bent portion of the first tubing.

To provide a pulseless linear flow in a rotary peristaltic pump, according to the present invention the cross-section of the outlet portion of the first tubing is smaller than the cross-section of at least some initial bent portion of the first tubing. This eliminates the occurrence of suction when an engagement element moves from one point to the other wherein the tubing would expand from a squeezed and flat configuration to a normal configuration. Such a suction which would cause discontinuity of flow is eliminated according to the teaching of the present invention by keeping the tubing flat during this portion of rotation.

Preferably, the resilient tube of the pumping means is pinched by having a flat configuration and, thus, a minimal internal volume from the last occlusion point in the circle until the point where an engagement element has fully released from the tubing and the outlet portion of the tubing continues in a direction tangential to the circle of rotation.

Moreover, a constricting element can be positioned at an inner side of the outlet portion of the first tubing facing the rotor and comprising a part-cyclic edge extending adjacent and essentially parallel to the periphery of the rotor so that the tubing remains flat as an engagement element moves away over the part-cyclic edge of the constricting element, and consequently the tubing cannot expand so as to cause undesired underpressure and negative pulse.

Finally, in order to achieve the above and further objects, in accordance with a third aspect of the present invention, there is provided an infusion pump device, comprising a pumping means having a fluid inlet which is adapted to be connected to a vial for taking fluid out of the vial and a fluid outlet which is adapted to be connected to an infusion catheter, wherein the pumping means is a rotary peristaltic pump means comprising a stationary flexible, preferably resilient, first tubing which includes an inlet portion defining the fluid inlet and an outlet portion defining the fluid outlet and is provided between both the inlet and outlet portions with a bent portion having an essentially part-cycle, preferably half-cycle, form, and a rotor which is provided with engagement elements for locally engaging the bent portion of the first tubing so as to squeeze it during rotation for a pumping action, wherein the cross-section of the inlet portion of the first tubing is larger than the cross-section of at least a major portion of the bent portion of the first tubing.

Accordingly, the initial upstream part of the tubing has a higher internal volume per length than the rest of the tubing so that any undesired underdelivery of flow caused by expansion of the tubing at its exit is compensated by some overdelivery of flow.

Preferably, the internal volume per length can be higher than the rest of the tubing also for a small upstream portion of the bent portion extending along a small number of degrees, in particular about 5 to 7 degrees.

Further preferred embodiments and modifications of the present invention are defined in the dependent claims.

BRIEF DESCRIPTION OF THE DRAWINGS

Preferred embodiments of the present invention will now be described with reference to the drawings, in which.

DETAILED DESCRIPTION

Figure 1:
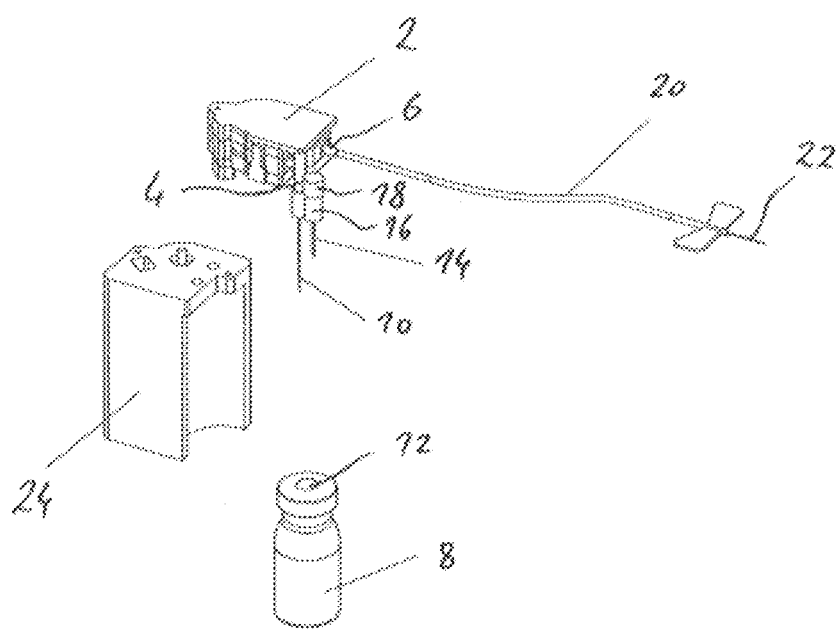
FIG. 1 is an exploded view of the infusion pump device according to a first preferred embodiment of the present invention.

FIGS. 1 to 4 show an infusion pump device according to a first preferred embodiment of the present invention which comprises a rotary peristaltic pumping mechanism 2 having a fluid inlet 4 and a fluid outlet 6 so that fluid is pumped from the fluid inlet 4 to the fluid outlet 6. As further shown in the FIGS. 1 to 4, a glass vial 8 which includes a drug fluid to be infused is provided to be coupled to the pumping mechanism 2 for taking the fluid (not shown here) out of the vial 8 by aspiration. For coupling the vial 8 to the pumping mechanism 2 there is provided an aspiration needle 10 which is connected to the fluid inlet 4 of the pumping mechanism 2 and is further adapted to puncture a rubber bung 12 closing the vial 8 (cf. FIGS. 2 and 3) so that the interior of the vial 8 is to be coupled via the aspiration needle 10 and the fluid inlet 4 to the pumping mechanism 2.

Figure 2:
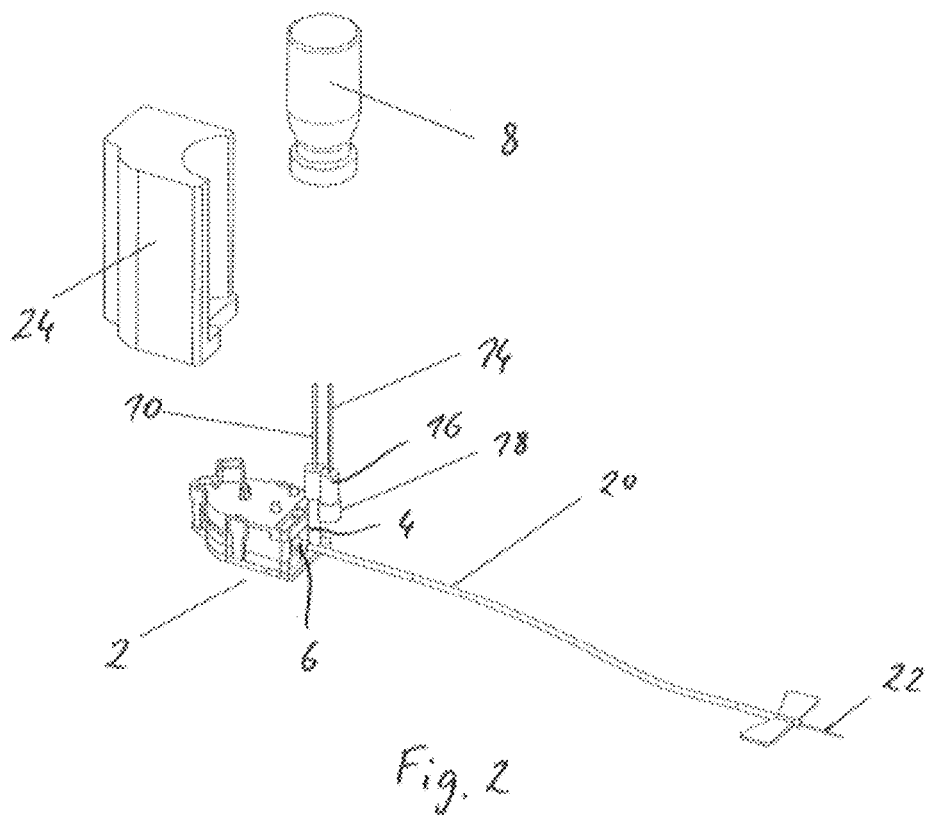
FIG. 2 is an exploded view of the infusion pump device according to the first embodiment of the present invention in an upside-down orientation over FIG. 1.

As shown in FIGS. 1 and 2, a further needle 14 is provided which is connected to a short small tube 16 whose inlet is provided with a filter 18. Preferably, this filter 18 is embodied as a hydrophobic membrane filter. The small tube 16 which supports the further needle 14 is mounted to the pumping mechanism 2, and the aspiration needle 10 and the further needle 14 are arranged essentially parallel one to another wherein the distance between both the needles 10, 14 is dimensioned so that the further needle 14 is adapted to puncture the bung 12 of the vial 8 at the same time when the aspiration needle 10 punctures the bung 12.

As further to be seen in the FIGS. 1 to 4, the fluid outlet 6 of the pumping mechanism 2 is provided for coupling an infusion tubing 20 with an infusion needle 22 mounted at its free end. The infusion tubing 20 and the infusion needle 22 form a subcutaneous infusion catheter wherein preferably the infusion needle 22 can be embodied as a so-called butterfly needle. Alternatively, the infusion catheter can be embodied as a so-called octopus for two or more simultaneous infusion sites. However, the infusion pump device according to the present invention can be used in all other infusion paths like intravenous, epidural etc.

Figure 3:
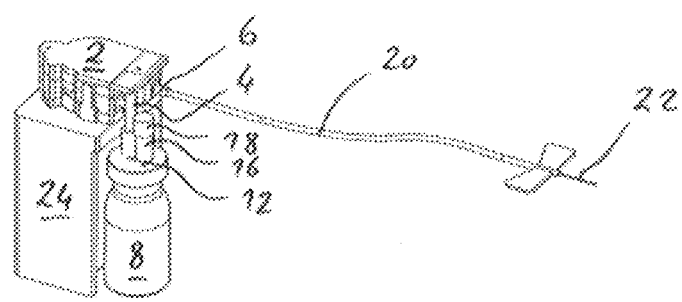
FIG. 3 shows the infusion pump device of FIG. 1 in an assembled configuration ready for infusion in the same orientation as FIG. 1.
Figure 4:
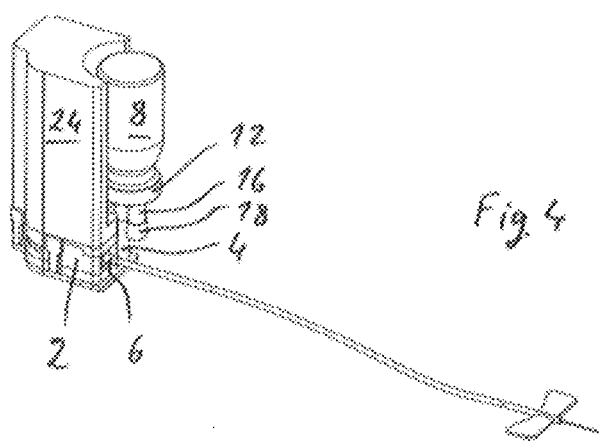
FIG. 4 shows the infusion pump device of FIG. 1 in an assembled configuration ready for infusion in the same orientation as FIG. 2.

As further shown in the FIGS. 1 to 4, there is provided a frame or casing 24 in particular for mounting the pumping mechanism 2 and the vial 8 (cf. FIGS. 3 and 4). The casing 24 is constructed such that stability in a vertical operating position for the vial 8 is given as shown in FIGS. 3 and 4. Preferably, the frame or casing 24 may comprise mounting means (not shown) which are adapted to ensure that both the needles 10, 14 puncture the bung 12 of the vial 8 at the same time through a single movement of the vial 8 when being mounted. Further, the casing 24 includes a small size controller (not shown) for ambulatory use which controller comprises electronics, screen, batteries, motor etc. and is adapted to control the pumping mechanism 2 and in particular its rotational speed and the infusion pressure. Downstream or upstream the pumping mechanism 2 the tubing can be provided with an ultrasonic air-in-line detector (not shown) which is adapted to warn the user if the vial 8 tilts and the aspiration needle 10 is unable to find any liquid. Furthermore, an inclination sensor (not shown) may be provided which electronically detects if the inclination of the vial 8 is more than a certain number of degrees, e.g. 45°, so as to then give a warning signal accordingly.

The pumping mechanism 2, the aspiration needle 10, the further needle 14 with the small tube 16 and the filter 18 and the subcutaneous infusion catheter defined by the infusion tubing 20 and the infusion needle 22 can commonly form a consumable component, wherein the entire pump-consumable-vial assembly can be worn for portable use.

The pumping mechanism 2 which is a rotary peristaltic mechanism here is preferably constructed in a similar manner as disclosed in e.g. U.S. Pat. No. 9,468,715, wherein preferably both the needles 10, 14 can commonly form one dual lumen.

The further needle 14, the small tube 16 and the filter 18 commonly form a unit which is provided as a means for controlling pressure inside the vial 8. This is necessary since the aspiration needle 10 does not allow air to pass through the bung 12 of the vial 8, and, as the drug fluid decreases in the vial 8 which is a closed container, the pressure also decreases according to the ideal gas law.

$$PV = nRT \qquad (1)$$

where P is the pressure of the gas, V is the volume of the gas, n is the amount of substance of gas (also known as number of moles), R is the ideal or universal gas constant (equal to the product of the Boltzmann constant and the Avogadro constant), and T is the temperature of the gas.

This implies that beyond a certain point, as long as there is always left the same amount n of air inside the vial 8 and since drug liquid is more or less incompressible, no further aspiration through the aspiration needle 10 is possible anymore in dependence on the aspiration capability of the resilient tubing. To avoid this, the unit formed by the further needle 14, the small tube 16 and the filter 18 takes care of venting the vial 8 so as to equalize the pressure inside and outside the vial 8 and, thus, to have the pressure inside the vial 8 always equal to atmospheric pressure. The hydrophobic membrane filter 18 is provided to prevent leakage in case of an accident and to purify air for anti-contamination. As already mentioned above, the further needle 14 can alternatively form a dual lumen together with the aspiration needle 10 in one part, or be embodied as a thin vented spike.

The first embodiment as described above with reference to the FIGS. 1 to 4 is suitable in particular for drugs which are not very much viscous.

Figure 5:
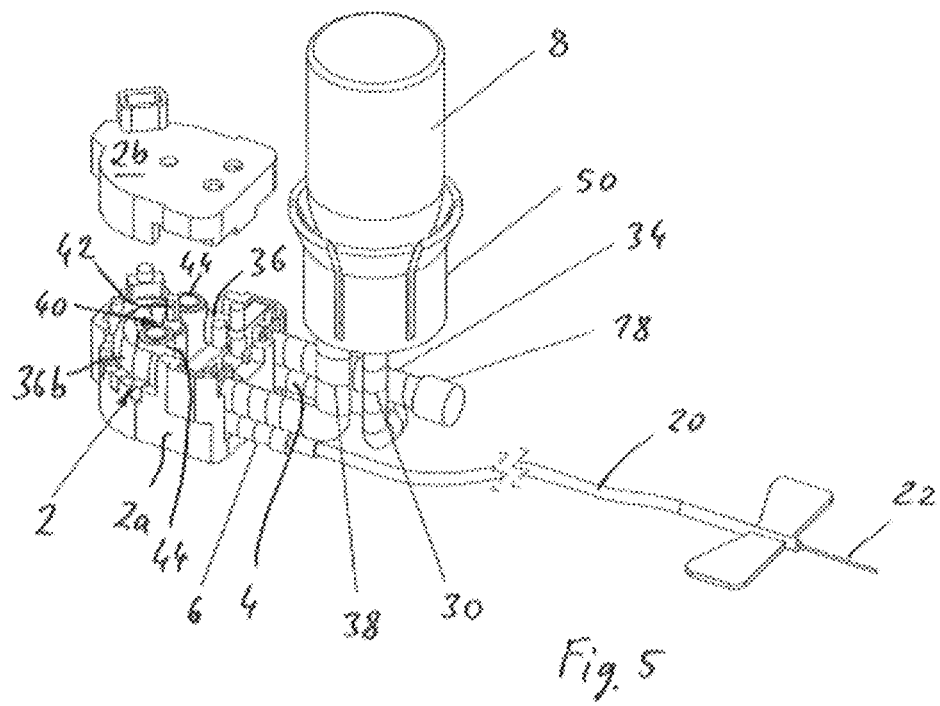
FIG. 5 is an exploded view of the infusion pump device according to a second preferred embodiment wherein the pumping mechanism additionally comprises an air compression layer.
Figure 6:
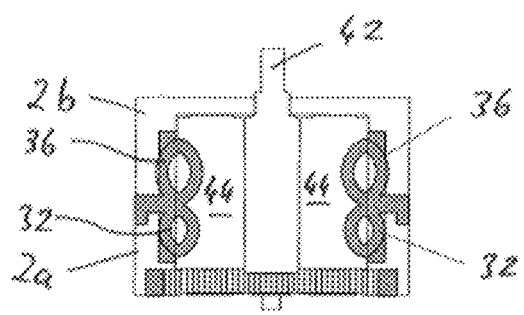
FIG. 6 is a cross-section view through the pumping mechanism comprising a dual resilient tubing arrangement and the provision of common fixing elements to fix the tubing to the walls of the casing.

FIGS. 5 and 6 show a second preferred embodiment which is more suitable for more viscous drugs wherein similar or same components are designated by the same reference numerals as already provided in the first embodiment. The rotary peristaltic pumping mechanism 2 comprises a housing consisting of a lower or base portion 2a and an upper or lid portion 2b wherein in FIG. 5 the upper portion 2b of the housing is shown in a removed position spaced from the lower portion 2a of the housing for a better illustration of internal components of the pumping mechanism 2. Although not shown, instead of needles as used in the first embodiment, thin connection spikes can be alternatively provided in the second embodiment which spikes have the same function as the needles 10, 14 of the first embodiment and must also be adapted to puncture the bung of the vial 8. Further, such spikes may be preferably embodied commonly as a dual lumen unit.

The aspiration needle or spike (not shown) is connected to an inlet tube 30 which again is connected to the fluid inlet 4 of the pumping mechanism 2. To the fluid inlet 4 connected is a first internal tubing 32 which comprises a bent portion having an U-shape and is arranged in a stationary manner within the lower portion 2a of the housing of the pumping mechanism 2 as shown in FIG. 6. At its downstream end the first tubing 32 is coupled to the fluid outlet 6 to which the infusion catheter is connected which consists of the infusion tubing 20 and the infusion needle 22. Preferably, the aspiration tube 30, the fluid inlet 4, the first tubing 32 and the fluid outlet 6 can integrally form a single-piece unit or tube. As further shown in FIG. 5, there is a first small air tube 34 whose inlet is provided with the filter 18 in a similar manner as the small tube 16 of the first embodiment. The tube 34 is coupled to a second internal tubing 36 which is arranged above the first internal tubing 32 in a stationary manner within the pumping mechanism 2 and comprises in the same manner a U-shaped bent portion as the first internal tubing 32. The second internal tubing 36 at its exit or outlet is coupled to a second air tube 38 which extends to the vial 8 and at its free end is provided with a needle or spike (not shown) which has the same function as the further needle 14 in the first embodiment. Since the first and second internal tubings 32 and 36 are arranged one above the other as shown in FIG. 6, the inlets of the first and second internal tubings 32 and 36 and the outlets of the first and second tubings 32, 36 each are arranged one above the other as it becomes clear from FIG. 5. Moreover, preferably the first air tube 34, the second internal tubing 36 and the second air tube 38 may integrally form a single-piece unit or tube.

Further, the pumping mechanism 2 includes a rotor 40 which rotates about a central axis or shaft 42 and comprises two engagement rollers 44 diametrically opposed to each other with respect to the axis or shaft 42. As in particular shown in FIG. 6, the engagement rollers 44 are provided so as to locally engage and squeeze both the first and second internal tubings 32, 36 at the same time during rotation of the rotor 40. Since the first internal tubing 32 is filled with the drug fluid taken out of the vial 8 into the fluid inlet 4 and to be guided out of the fluid outlet 6 into the infusion tubing 20, the local squeezing of the first internal tubing 32 by an engagement roller 44 during rotation of the rotor 40 results in a pumping operation effecting the pumping of the fluid from the fluid inlet 4 to the fluid outlet 6 of the pumping mechanism 2. A similar effect is achieved along the second internal tubing 36 above the first internal tubing 32. Namely, since the second internal tubing 36 defines an air line, the local squeezing of the second internal tubing 36 by an engagement roller 44 results in a pumping operation by which air taken from the outside through the filter 18 and the first air tube 34 is pumped and, thus, pressed through the second internal tubing 36 and the second air tube 38 into the vial 8.

Moreover, as shown in FIG. 5, the pump infusion device according to the second embodiment further comprises a vial adapter 50 which is provided as a vial retention for accompanying and mounting the head portion of the vial 8 including the bung with the vial 8 being orientated upside down.

So for pressurizing air into the vial 8 in the second preferred embodiment according to FIGS. 5 and 6, the second internal tubing 36 is provided in the pumping mechanism 2 which tubing is resilient and to be squeezed by the same engagement roller 44 as the first internal tubing 32 which is also resilient and arranged below the second internal tubing 36 in the pumping mechanism 2.

Accordingly, the first internal tubing 32 defines a fluid pumping layer or level, and the second internal tubing 36 defines an air pumping or pressurizing layer or level.

Figure 7:
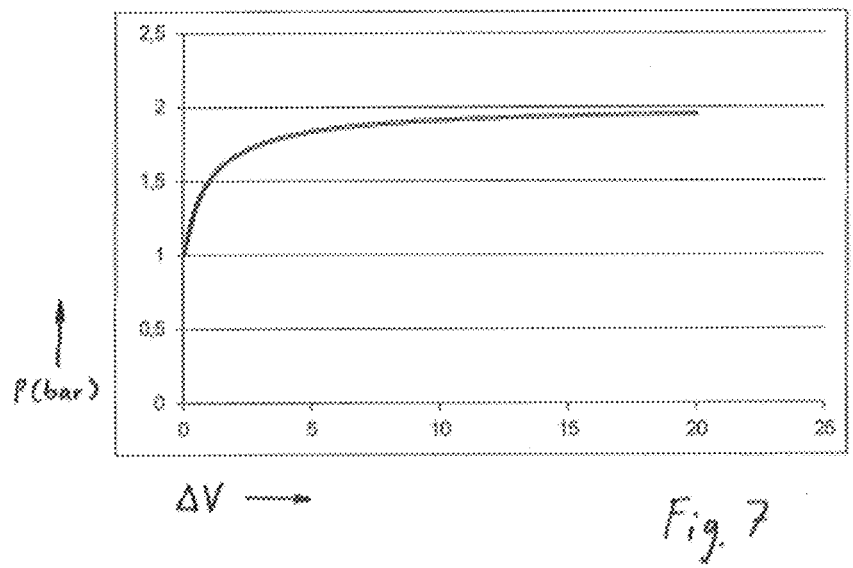
FIG. 7 shows a pressure curve.

As further seen in FIG. 6, the cross-section of the second internal tubing 36 is larger than the cross-section of the first internal tubing 32, wherein concretely the cross-section of the second internal tubing 36 is about double of the cross-section of the first internal tubing 32. This causes the volume of air forced due to the rotation of the rotor 40 out of the pumping mechanism 2 into the vial 8 to be about twice as the volume of the fluid pumped out of the vial 8 into the infusion tubing 20 by the pumping mechanism 2 due to the rotation of the rotor 40. When double the volume of air is introduced compared to the volume of fluid expelled, on the basis of the ideal gas law according to the aforementioned equation (1), the pressure in the vial 8 will soon become twice as atmospheric pressure (2 bar) as shown by an asymptotic course of the curve in FIG. 7. As a result, the aspiration of drugs with higher viscosity such as immunoglobulins or DuoDopa® is easily achieved with higher accuracy. The precise relationship for this scenario is given on the basis of the aforementioned equation (1) as follows:

$$P = nRT/V = Vp/V \quad (2)$$

where Vp stands as equivalent of nRT for the volume of air V at atmospheric pressure, and V is the volume occupied by the air in the vial 8. As the final relationship for the volume ΔV of fluid removed it is given $$P = (V + 2\Delta V)/(V + \Delta V) \quad (3)$$

wherein in the numerator the initial volume of air V plus the increase in mass per volume by double the occupied volume 2ΔV is given due to the double cross-section of the second internal tubing 36 and in the denominator the increase in volume of air after removal of an equal volume of fluid ΔV is given under the assumption that the vial 8 defines a closed system. As illustrated in FIG. 7, the curve starts with a pressure in the vial 8 equal to the atmospheric pressure (1 bar) and rises rapidly to an asymptote at 2 bar. Of course, a pressure other than 2 bar can be attained by giving the cross-sections of the second and first internal tubings 36, 32 (cf. FIG. 6) a different ratio, i.e. other than 2.

The pumping mechanism 2 which is also provided at its fluid inlet 4 with a pressure sensor operating as an upstream occlusion sensor (not shown here) can run more rapidly in case the pressure sensor detects the occurrence of low pressure in the fluid, and then run at the correct rate of infusion when the pressure of fluid at the fluid inlet 4 reaches a certain threshold beyond which the dosing accuracy can be considered satisfactory. In a modification of this system, the pumping mechanism 2 is running at a speed taken from a table of measurements or calculations proportional to the pressure of the fluid at the fluid inlet 4 (upstream pressure) so as to attempt to cover the loss of fluid per revolution of the rotor 40 with more revolutions of the rotor 40 in the pumping mechanism 2.

Moreover, the infusion pump device preferably comprises an infusion pressure sensor operating as a downstream occlusion sensor (not shown here) at the fluid outlet 6 of the pumping mechanism 2 or at the infusion tubing 20 (downstream occlusion) to monitor an occurrence of kinking or blocking of the infusion tubing 20 and in case of such an occurrence to give an alarm.

For drugs to be infused in sequence, such as immunoglobulin and Baxter's hyaluronic HyQvia®, there may be provided a drug selection valve (not shown here) on the intake (a second needle with a tube extending beyond the main tube with direct aspiration) and an appropriate controller for controlling the drug selection valve and the pumping mechanism 2 in accordance with a particular pump program and protocol.

In the FIGS. 2, 4 and 5, the vial 8 is shown in an operational position which is the most common and, thus, normal operational position where the vial 8 is inverted with its top down so that it is sufficient to provide both the needles 10, 14 or the corresponding spikes with more or less the same length which may be relatively short. However, if the vial 8 is arranged with its head portion including the bung 12 upright the length of the needles 10, 14 or the corresponding spikes must be different wherein the aspiration needle 10 or the corresponding aspiration spike has a longer length so as to reach the bottom of the vial 8, whereas the further needle 14 or the corresponding spike needs to be shorter so as to exit just behind the bung 12 where the air volume is created. Further, as already mentioned above, an additional inclination sensor can be provided to monitor the orientation of the vial 8 so that the vial 8 is assured to be arranged in an essentially vertically orientation, and is adapted to give a warning signal in case the vial 8 has been moved into an inclined or tilted orientation by a number of degrees exceeding a predetermined threshold defining a certain number of degrees.

Whereas in the above described second embodiment the pumping mechanism 2 is a rotary peristaltic pumping mechanism, alternatively there can be provided a linear peristaltic pumping mechanism including two parallel tubings which are engaged by the same cam followers and can have the same effect as it may also be the case with diaphragm pumps or other pumps having dual infusion capability.

Figure 8:
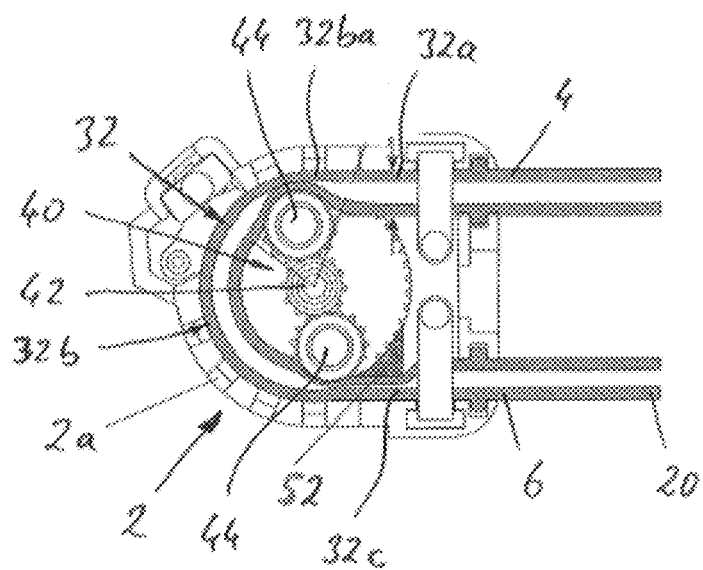
FIG. 8 is a top view onto a pumping mechanism of an infusion pump device according to a third preferred embodiment of the present invention with the cover of its casing being removed.

FIG. 8 shows an infusion pump device according to a third embodiment which differs from the second embodiment according to FIG. 5 in a modification of the fluid pumping layer so as to realize a pulseless infusion. As seen from FIG. 8, the first internal tubing 32 comprises an inlet portion 32*a*, the already aforementioned U-shaped bent portion 32*b* and an outlet portion 32*c* connected to the outlet fluid 6. As further to be seen from FIG. 8, the cross-section of the inlet portion 32*a* and a short upstream portion 32*ba* of the bent portion 32*b* of the first internal tubing 32 is larger than the cross-section of the rest of the first internal tubing 32 wherein the upstream portion 32*ba* of the bent portion 32*b* of the first internal tubing 32 follows the input portion 32*a* of the first internal tubing 32 in direction of rotation of the rotor 40 and extends along a small number of about 5 to 7 degrees. In other words, the inlet portion 32*a* and the upstream portion 32*ba* of the bent portion 32*b* of the first internal tubing 32 is wider than the rest of the first internal tubing 32 so that a larger volume per length of the resilient first internal tubing 32 at the upstream start of infusion length is created in contrast to a standard volume per length along the rest of the bent portion 32*b* of the first internal tubing 32. So, overpressure is built up at the start of a 180° infusion cycle so as to compensate loss of infusion resulting in a negative infusion pulse at the end of the previous ending cycle when the engagement roller 44 disengages from the first internal tubing 32 which then expands to its standard dimension.

As further shown in FIG. 8, the cross-section of the outlet portion 32*c* of the first internal tubing 32 is smaller than the cross-section of the bent portion 32*b* of the first internal tubing 32. So, along the outlet portion 32*c* of the first internal tubing 32 a smaller volume per length is created in contrast to the standard volume per length along the bent portion 32*b*. With respect thereto, a constricting element 52 made of elastic material is positioned at an inner side of the outlet portion 32*c* of the first internal tubing 32 facing the rotor 40 and comprises a part-cyclic edge 52*a* extending adjacent and essentially parallel to the periphery of the body of the rotor 40. This eliminates the occurrence of suction when an engagement roller 44 disengages from the point where the tubing 32 would expand from a squeezed and flat configuration to a normal configuration. Such a suction which would cause discontinuity of flow is eliminated by keeping the tubing 32 flat during this portion of rotation of the rotor 40 which defines an upstream portion of the outlet portion 32*c* of the first internal tubing 32. The tubing 32 is pinched by having a squeezed and flat configuration and, thus, a minimal internal volume from the last occlusion point in the circle until the point where the engagement roller 44 has fully released from the tubing 32. So, the tubing 32 remains flat as an engagement roller 44 moves away over the part-cyclic edge 52a of the constricting element 52, and consequently the tubing 32 cannot expand so as to cause undesired underpressure and negative pulse.

Finally, it is to be added here that the infusion pump device may also include telemedicine services as described in e.g. U.S. Pat. No. 8,551,038.

The invention claimed is:

1. An infusion pump device comprising:
a pumping means having a fluid inlet which is adapted to be connected to a vial for taking fluid out of the vial and a fluid outlet which is adapted to be connected to an infusion catheter, wherein the pumping means is a rotary peristaltic pump means comprising:
a stationary flexible first tubing which includes an inlet defining the fluid inlet and an outlet defining the fluid outlet and is provided between the fluid inlet and the fluid outlet with a bent portion having an essentially part-cycle form, and
a rotor which is provided with engagement elements for locally engaging the bent portion of the first tubing so as to squeeze it during rotation for a pumping action; and
a controlling means which is adapted to be connected to the vial and to control pressure inside the vial so as to avoid occurrence of underpressure at the fluid inlet, wherein the controlling means comprises:
an air line having an air inlet and an air outlet, wherein the air outlet is adapted to be connected to the vial for delivering air taken up through the air inlet into the vial, and
a stationary flexible second tubing which includes an inlet defining the air inlet and an outlet defining the air outlet so as to define the air line and is provided between the air inlet and the air outlet with a bent portion having an essentially part-cycle form, wherein the rotor is provided with engagement elements for locally engaging the bent portion of the second tubing so as to squeeze it during rotation, wherein the cross-section of the second tubing is larger than the cross-section of the first tubing.

2. The device according to claim 1, wherein the controlling means comprises a spike or a needle which is adapted to puncture a bung closing the vial.

3. The device according to claim 1, wherein the needle is coupled to the air outlet.

4. The device according to claim 1, wherein the air line comprises a filter.

5. The device according to claim 4, wherein the filter is provided at the air inlet.

6. The device according to claim 4, wherein the filter is a hydrophobic membrane filter.

7. The device according to claim 1, wherein the first tubing and the second tubing are arranged one above the other.

8. The device according to claim 7, wherein the inlets of the first and second tubings and the outlets of the first and second tubings each are arranged one above the other.

9. The device according to claim 1, wherein the cross-section of the second tubing is essentially twice as large as the cross-section of the first tubing.

10. The device according to claim 1, wherein the engagement elements of the rotor are adapted for simultaneously engaging both the first and second tubings.

11. The device according to claim 1, further comprising a casing or frame to which the pumping means and the controlling means are mounted, wherein the casing or frame includes further means for mounting at least a vial so that the controlling means and the fluid inlet of the pumping means are simultaneously connected to the vial through a single movement of the vial when being mounted.

12. The device according to claim 1, further comprising sensor means adapted to monitor the air pressure in the vial and/or the flow of fluid or the occurrence of any blockage and/or to monitor the occurrence of air bubbles within the pumping means and/or the infusion catheter and/or to monitor the orientation of the vial so that the vial is assured to be arranged in an essentially vertical orientation.

13. The device according to claim 1, wherein the fluid inlet comprises a spike or a needle which is adapted to puncture a bung closing the vial.

14. The device according to claim 1, wherein at least one of the first tubing and the second tubing is resilient.

15. The device according to claim 1, wherein the bent portion of at least one of the first tubing and the second tubing has a half-cycle form.

16. An infusion pump device comprising:
a pumping means having a fluid inlet which is adapted to be connected to a vial for taking fluid out of the vial and a fluid outlet which is adapted to be connected to an infusion catheter, wherein the pumping means is a rotary peristaltic pump means comprising:
a stationary flexible first tubing which includes an inlet portion defining the fluid inlet and an outlet portion defining the fluid outlet and is provided between both the inlet and outlet portions with a bent portion having an essentially part-cycle form, wherein the cross-section of the outlet portion of the first tubing is smaller than the cross-section of at least the bent portion of the first tubing, and
a rotor which is provided with engagement elements for locally engaging the bent portion of the first tubing so as to squeeze it during rotation for a pumping action; and
a controlling means adapted to be connected to the vial and to control pressure inside the vial so as to avoid occurrence of underpressure at the fluid inlet, the controlling means comprising:
an air line having an air inlet and an air outlet, wherein the air outlet is adapted to be connected to the vial for delivering air taken up through the air inlet into the vial, and
a stationary flexible second tubing which includes an inlet defining the air inlet and an outlet defining the air outlet so as to define the air line and is provided between the air inlet and the air outlet with a bent portion having an essentially part-cycle form, wherein the rotor is provided with engagement elements for locally engaging the bent portion of the second tubing so as to squeeze it during rotation, wherein the cross-section of the second tubing is larger than the cross-section of the first tubing.

17. The device according to claim 16, further comprising a constricting element which engages a wall portion of the outlet portion of the first tubing for reducing its cross-section.

18. The device according to claim 17, wherein the rotor comprises an essentially cylindric body and the constricting element is positioned at an inner side of the outlet portion of the first tubing facing the rotor and comprises a part-cyclic edge extending adjacent and essentially parallel to the periphery of the body of the rotor.

19. The device according to claim 17, wherein the constricting element at least at a portion engaging the wall portion of the outlet portion of the first tubing is made of elastic material.

20. The device according to claim 16, wherein at least one of: the first tubing is resilient and the bent portion has a half-cycle form.

\* \* \* \* \*